(12) United States Patent
Liu et al.

(10) Patent No.: US 7,745,505 B2
(45) Date of Patent: Jun. 29, 2010

(54) PHOTOINITIATORS AND UV-CROSSLINKABLE ACRYLIC POLYMERS FOR PRESSURE SENSITIVE ADHESIVES

(75) Inventors: Yuxia Liu, Dayton, NJ (US); Darwin Scott Bull, Hillsborough, NJ (US)

(73) Assignee: Henkel AG & Co. KGaA, Duesseldorf (DE)

( * ) Notice: Subject to any disclaimer, the term of this patent is extended or adjusted under 35 U.S.C. 154(b) by 157 days.

(21) Appl. No.: 11/024,570

(22) Filed: Dec. 29, 2004

(65) Prior Publication Data
US 2006/0142408 A1 Jun. 29, 2006

(51) Int. Cl.
*C08F 130/08* (2006.01)
*C08F 220/10* (2006.01)

(52) U.S. Cl. .......................... 522/34; 522/35; 522/905; 522/152; 522/148; 526/279; 526/301; 526/302; 526/329.2

(58) Field of Classification Search .................... 522/34, 522/35, 63, 120, 172, 173, 182, 905, 148, 522/152
See application file for complete search history.

(56) References Cited

U.S. PATENT DOCUMENTS

| | | | |
|---|---|---|---|
| 3,214,492 A | 10/1965 | Tocher | |
| 3,322,818 A | 5/1967 | Hanze et al. | |
| 3,429,852 A | 2/1969 | Skoultchi | |
| 4,144,157 A | 3/1979 | Guse et al. | |
| 4,148,987 A * | 4/1979 | Winey | 526/316 |
| 4,496,447 A * | 1/1985 | Eichler et al. | 522/34 |
| 4,604,439 A * | 8/1986 | Colvin et al. | 526/288 |
| 4,737,559 A | 4/1988 | Kellen et al. | |
| 5,068,291 A | 11/1991 | Gallaway et al. | |
| 5,073,611 A | 12/1991 | Rehmer et al. | |
| 5,128,386 A | 7/1992 | Rehmer et al. | |
| 5,206,417 A | 4/1993 | Boettcher et al. | |
| 5,223,645 A | 6/1993 | Barwich et al. | |
| 5,264,533 A | 11/1993 | Rehmer et al. | |
| 5,292,915 A | 3/1994 | Boettcher et al. | |
| 5,294,688 A | 3/1994 | Rehmer et al. | |
| 5,506,279 A * | 4/1996 | Babu et al. | 522/34 |
| 5,532,112 A * | 7/1996 | Kohler et al. | 430/281.1 |
| 5,536,759 A | 7/1996 | Ramharack et al. | |
| 5,741,543 A | 4/1998 | Winslow | |
| 5,804,610 A * | 9/1998 | Hamer et al. | 522/182 |
| 5,859,084 A | 1/1999 | Schroder | |
| 6,242,504 B1 | 6/2001 | Meyer-Roscher et al. | |
| 6,642,298 B2 | 11/2003 | Foreman et al. | |
| 2003/0088031 A1 | 5/2003 | Husemann et al. | |

FOREIGN PATENT DOCUMENTS

| | | |
|---|---|---|
| DE | 27 43 979 | 4/1979 |
| EP | 0 246 848 B1 | 3/1992 |
| WO | WO 03/033544 | 4/2003 |

* cited by examiner

*Primary Examiner*—Susan W Berman
(74) *Attorney, Agent, or Firm*—James E. Piotrowski

(57) ABSTRACT

UV-crosslinkable acrylic hotmelt pressure sensitive adhesives comprising acrylic and vinyl monomers, and a polymerizable UV photoinitiator. The photoinitiator comprises a spacer comprising both ethylene oxide and urethane, or urea, carbonate, or siloxane functional groups. The ethylene oxide is directly bonded to the chromophore (e.g., benzophenone) moiety, while the urethane (or urea, carbonate, siloxane) is closely linked to the polymerizable moiety (e.g., styrenic C=C double bond).

13 Claims, No Drawings

PHOTOINITIATORS AND UV-CROSSLINKABLE ACRYLIC POLYMERS FOR PRESSURE SENSITIVE ADHESIVES

FIELD OF THE INVENTION

The invention relates to polymerizable UV photoinitiators and UV-crosslinkable acrylic polymers that are particularly useful in the manufacture of hotmelt pressure sensitive adhesives.

BACKGROUND OF THE INVENTION

Hotmelt pressure sensitive adhesives (HMPSAs) are compositions that combine the properties of hotmelt adhesives with those of pressure sensitive adhesives. Hotmelt adhesives are solids at room temperature, melt at elevated temperatures to coat on a substrate, and regain their solid form on cooling. Pressure sensitive adhesives are aggressive and permanently tacky at room temperature and adhere to surfaces by application of light finger pressure. The combination of these properties provides compositions that melt at elevated temperatures and cool to form a permanently tacky solid coating that adheres on contact. These compositions are commonly applied to various substrates, such as paper, fabric, metal, and plastic films that are then converted into a large number of different products, especially pressure sensitive adhesive tapes and labels. These pressure sensitive adhesive products have a broad field of application in the automobile industry, e.g., for fastening or sealing, in the pharmaceutical industry, e.g., for bandages or transdermal drug delivery systems, or in the packaging industry, e.g., for sealing, bonding or labeling.

A good workable HMPSA must exhibit high cohesive strength at room temperature, low shrinkage on substrates, retention of pressure sensitive properties during storage and use, and a relatively fluid viscosity at typical coating temperatures (e.g., from about 80° C. to about 180° C.). Although very low molecular weight polymers will yield hotmelt adhesives with sufficient fluidity, the resulting adhesives lack cohesive strength. Very high molecular weight polymers give better cohesive strength, but are too viscous at the common application temperatures to be easily coatable on substrates. They must be extended with a high proportion of low molecular weight oils or resins to reduce the viscosity. The addition of low molecular weight oils or resins in turn detracts from the cohesive strength and heat resistance. In order to increase the cohesion, therefore, a high molecular weight is essential. To avoid these problems, polymers of moderate molecular weight have been made with various functional groups which undergo crosslinking reactions by actinic radiation. In this manner, the cohesion of acrylic PSAs can be raised by means of sufficient crosslinking.

There is an ongoing demand and a continuing need in the art for UV-crosslinkable acrylic polymers that are hot melt processable, as well as methods of manufacturing such polymers. The current invention addresses this need by providing polymers that are functionalized with pendant UV photoinitiators and, following the coating operation, are crosslinked on the substrates as acrylic HMPSAs.

SUMMARY OF THE INVENTION

The invention provides photoinitiators, acrylic polymers comprising a photoinitiator, and UV curable adhesives comprising acrylic polymers.

One aspect of the invention is directed to photoinitiators having the structural formula

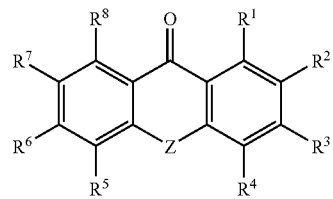

or

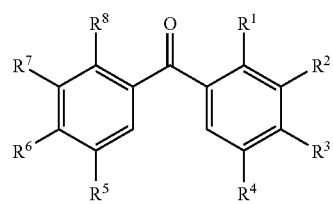

or

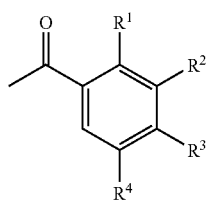

where

Z is S, O, $CH_2$, or NH, $R^{1-8}$ are independently H, Cl, Br, I, F, $C_{1-24}$ alkoxy, $C_{1-24}$ alkyl, or aryl; and wherein at least one of $R^{1-8}$ must comprise a —W—X—Y group, where W is a $C_{1-12}$ alkylene or $C_{1-12}$ oxyalkylene, X is carbonate, urethane, urea, tetramethyldisiloxane or a combination thereof, and Y is —$R^9$—C($R^{10}$)=$CH_2$, where $R^9$ is a linear or branched $C_{2-10}$ alkylene or $C_{2-10}$ oxyalkyle or arylene or derivative thereof, and $R^{10}$ is H or $CH_3$.

Particularly preferred embodiments are photoinitiators having the following structural formula:

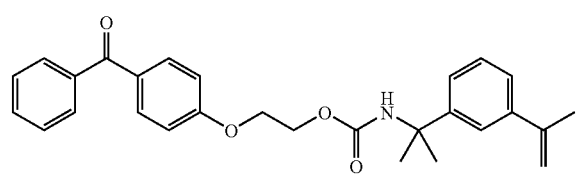

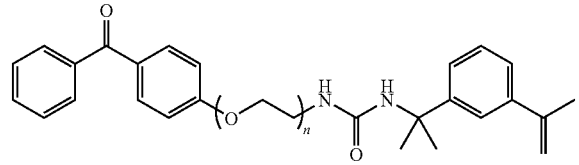

where n=1-12 and

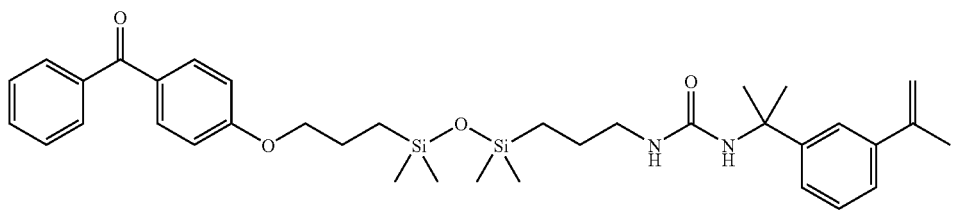

Another aspect of the invention is directed to UV curable acrylic polymers comprising the photoinitiators described herein. The acrylic polymers of the invention will typically comprise from about 70 to about 95 parts by weight of acrylic or methacrylic acid derivative of the formula $CH_2=CH(R^1)(COOR^2)$, where $R^1$ is H or $CH_3$ and $R^2$ is a $C_{1-20}$ alkyl chain, 0 to about 30 parts by weight of an acrylic or methacrylic acid derivative of the formula $CH_2=CH(R^1)(COOR^2)$, where $R^1$ is H or $CH_3$ and and $R^2$ is an hydroxyl functional $C_{1-20}$ alkyl chain, 0 to about 20 parts by weight of an acrylic or vinyl compound containing a carboxy or anhydride functional group, 0 to about 30 parts by weight of acrylic or vinyl compounds containing an amine, amide, urethane, epoxide or isocyanate functional group, and from about 0.01 to about 15 parts, more preferably from about 0.1 to abut 5 parts, by weight of the photoinitiator described herein.

Yet another aspect of the invention is directed to UV crosslinkable hot melt pressure sensitive adhesives comprising the acrylic polymers described herein.

The adhesive may be used in the manufacture of articles such as, for example, industrial and medical tapes, and articles of manufacture comprising the adhesives are encompassed by the invention.

DETAILED DESCRIPTION OF THE INVENTION

The invention provides the art with acrylic polymers comprising photoinitiators bound to the polymer chain. The polymerizable photoinitiators contain both C=C double bond and UV reactive chromophore of aromatic ketone. The photoinitiator comprises a spacer containing both ethylene oxide and urethane, urea, carbonate or siloxane functional groups. The ethylene oxide is directly bonded to the chromophore (e.g., benzophenone) moiety, while the urethane, urea, carbonate or siloxane is closely linked to the polymerizable moiety, e.g., acrylic or styrenic C=C double bond.

The choice and relative amount of the specific acrylic and vinyl monomers making up the acrylic polymers used in the HMPSAs of this invention depend upon the desired final properties and contemplated end uses of the adhesives. The choice of which acrylic and vinyl monomers and their relative amounts in the final composition to achieve the desired properties are within the expertise of those skilled in the art.

In one embodiment of the invention, the acrylic polymers used are those having the following composition or those that can be prepared by polymerizing a monomer mixture comprising the following monomers or components: (a) from about 70 to about 95 parts by weight of acrylic or methacrylic acid derivative of the formula $CH_2=CH(R^1)(COOR^2)$, where $R^1$ is H or $CH_3$ and $R^2$ is a $C_{1-20}$ alkyl chain, (b) 0 to about 30 parts by weight of an acrylic or methacrylic acid derivative of the formula $CH_2=CH(R^1)(COOR^2)$, where $R^1$ is H or $CH_3$ and $R^2$ is an hydroxyl functional $C_{1-20}$ alkyl chain, (c) 0 to about 20 parts by weight of an acrylic or vinyl compound containing a carboxy or anhydride functional group, (d) 0 to about 30 parts by weight of acrylic or vinyl compounds containing an amine, amide, urethane, epoxide or isocyanate functional group and (e) from about 0.01 to about 15 parts, more preferably from about 0.1 to abut 5 parts, by weight of a photoinitiator, which is described in more detail herein below.

For the process of the invention the monomers of components (a), (b), (c), (d), and (e), where appropriate, are converted by polymerization into the acrylic polymers. For polymerization the monomers are chosen such that the resulting copolymers can be used as HMPSAs, especially such that the resulting copolymers possess pressure sensitive adhesive properties in accordance with the "Handbook of Pressure Sensitive Adhesive Technology" by Donatas Satas (van Nostrand, N.Y. 1989). For these applications the static glass transition temperature of the resulting copolymers will advantageously be below about 25° C.

Examples of acrylic and/or methacrylic acid derivatives useful as component (a) include methyl acrylate, methyl methacrylate, n-butyl acrylate, n-pentyl acrylate, n-hexyl acrylate, n-heptyl acrylate, and n-octyl acrylate, n-nonyl acrylate, and their corresponding branched isomers, such as 2-ethylhexyl acrylate, and isooctyl acrylate. These monomers, especially the branched isomers, are able to undergo UV-initiated radical crosslinking or coupling reactions (H-abstraction) with the photoinitiators or UV-reactive functional monomers, which are defined in more detail below.

Examples of acrylic and/or methacrylic acid derivatives useful as component (b) include hydroxyethyl acrylate, hydroxypropyl acrylate, hydroxybutyl acrylate, and their corresponding methacrylates. It is possible to use vinyl compounds, instead of acrylates or methacrylates, such as vinyl acetate, styrene, α-methyl styrene, ethyl vinyl ether, acrylonitrile, and vinyl chloride. Vinyl monomers from the following exemplified groups may be used optionally as component (b): vinyl esters, vinyl ethers, vinyl halides, vinylidene halides, vinylpyridine, vinyl compounds containing aromatic rings and heterocycles in the α position.

Examples of suitable acrylic or vinyl monomers containing carboxylic acid or anhydride functional groups useful as component (c) include acrylic acid, methacrylic acid, itaconic acid, maleic anhydride, itaconic anhydride, 4-(methacryloyloxyethyl)trimellitic anhydride and the like.

Examples of suitable acrylic or vinyl compounds useful as component (d), capable in particular of a hydrogen-abstraction reaction with UV photoinitiators or other UV reactive functional group, include amine, amide, and benzylic compounds of the following formula

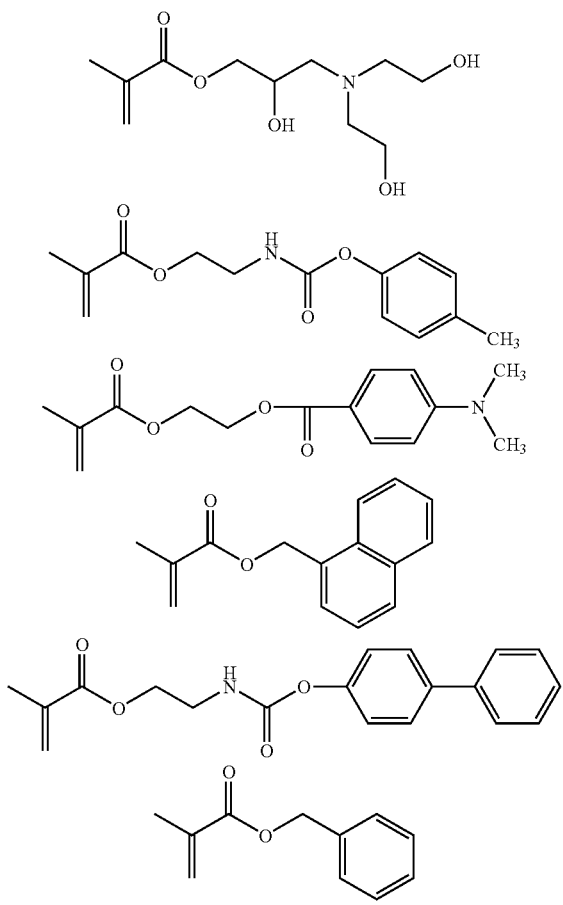

Other examples of suitable acrylic or vinyl monomers useful as component (d) are acrylamides, N-vinyl formamide, vinyl pyridine, and t-octyl acrylamide, 1-vinyl-2-pyrrolidinone (NVP), 2-(tert-butylamino)ethyl methacrylate (t-BEAM). Additionally, as monomers for component (d) are isocyanate-functionalized monomers, such as MOI, m-TMI®; or epoxidized monomers, such as glycidyl methacrylate; or more generally, all monomers containing a functional group able to enter into a chemical reaction with UV photoinitiators.

Examples of suitable vinyl or acrylic compounds containing photoinitiators useful as component (e), capable of undergoing UV-activated crosslinking reaction through intermolecular hydrogen-abstraction and then radical coupling reaction, include compounds of the following formula I, II and III:

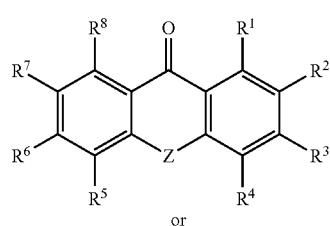
(I)

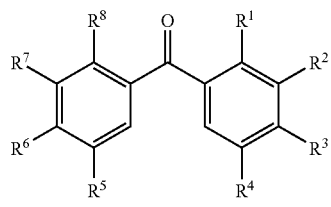
(II)

or

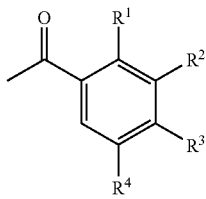
(III)

where

Z is S, O, $CH_2$, or NH, $R^{1-8}$ are independently H, Cl, Br, I, F, $C_{1-24}$ alkoxy, $C_{1-24}$ alkyl, or aryl; and wherein at least one of $R^{1-8}$ must comprise a —W—X—Y group, where W is a $C_{1-12}$ alkylene or $C_{1-12}$ oxyalkylene, X is carbonate, urethane, urea, tetramethyldisiloxane or a combination thereof, and Y is —$R^9$—C($R^{10}$)=$CH_2$, where $R^9$ is a linear or branched $C_{2-10}$ alkylene or $C_{2-10}$ oxyalkyle or arylene or derivative thereof, and $R^{10}$ is H or $CH_3$.

A preferred photoinitiator for use as component (e) is represented by the structural formula (IIA):

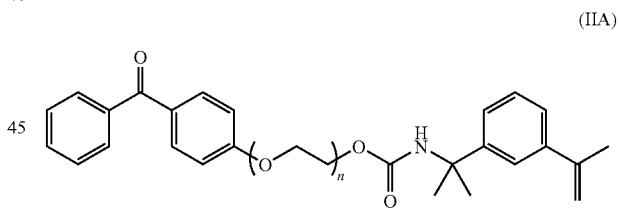
(IIA)

where n=1-12, preferably n=1.

Another preferred photoinitiator for use as component (e) is represented by the structural formula (IIIA):

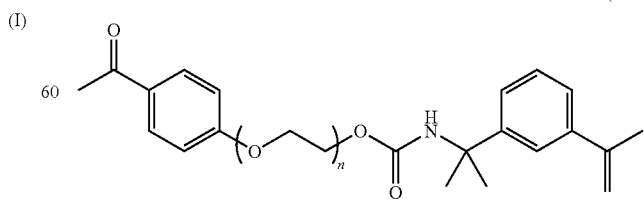
(IIIA)

where n=1-12, preferably n=1.

Another preferred photoinitiator for use as component (e) is represented by the structural formula (IIB):

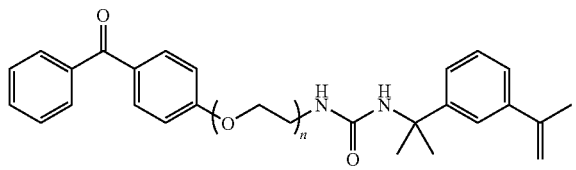

(IIB)

where n=1-12, preferably n=1.

Yet another preferred photoinitiator for use as component (e) is represented by the structural formula (IIC):

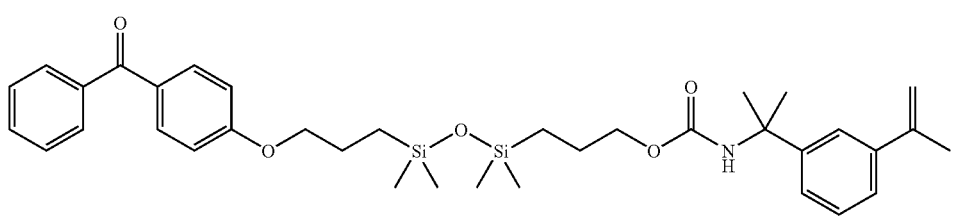

(IIC)

Yet another preferred photoinitiator for use as component (e) is represented by the structural formula (IID):

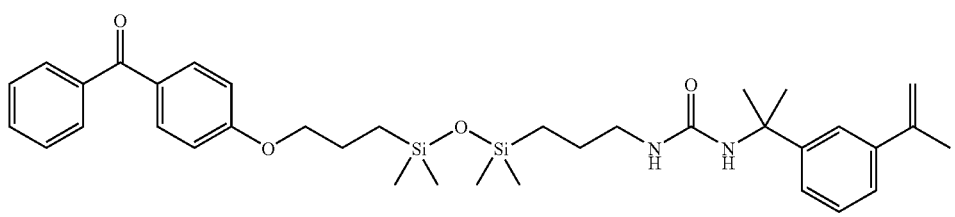

(IID)

In general, UV photoinitiators may be subdivided into Norrish Type I and Type II photoinitiators. Examples of both classes include benzophenone, acetophenone, benzil, benzoin, hydroxyalkylphenone, phenyl cyclohexyl ketone, anthraquinone, thioxanthone, triazine or fluorenone derivatives, and the like.

Compounds referred to as Norrish Type I photoinitiators are those which on exposure to light decompose in accordance with a Norrish Type I reaction. It is conventionally the photofragmentation of a carbonyl compound, in which the bond to a carbon atom α to the carbonyl group is cleaved radically (α-cleavage) to produce an acyl radical and an alkyl radical.

For the purposes of the invention, the Norrish photoinitiators also include those where instead of the carbonyl group another functional group is present and where cleavage relates to the bond between this group and an α carbon atom.

Norrish Type II photoinitiators break down on exposure to light in accordance with a Norrish Type II reaction with hydrogen abstraction; this is an intramolecular reaction.

In the case of aliphatic ketones, a hydrogen may be eliminated from the γ-position to one corresponding to the functional group shown above.

The Type I initiators include, in particular, aromatic carbonyl compounds, such as benzoin derivatives, benzil ketals and acetophenone derivatives. Type II photoinitiators are, in particular, aromatic ketones, such as benzophenone, benzil or thioxanthones, for example. For further details see, for example, Römpp Lexikon Chemie-Version 2.0, Stuttgart/New York: Georg Thieme Verlag 1999.

Furthermore, there also exist photoinitiators based on triazine, hexaarylbisimidazole, and dye. A good overview is given here in Chemistry & Technology of UV & EB Formulation for Coatings, Inks & Paints, Vol. 5, by Dowling, Pappas, Monroe, Carroy, Decker, ed. by P K T Oldring, Sita Technology, London, England.

The amount of component (e) that is incorporated into the polymeric chain must be sufficient to provide enough crosslinking to maintain an excellent balance of tack, peel adhesion, and cohesive strength for the end use contemplated. This amount will be dependent on the polymeric compositions, the source of radiation, the dosage of radiation received, and the thickness of the adhesive coating on the substrate. In general, this amount will be in the range of 0.01 to 15 parts per hundred parts of the acrylic or vinyl monomers, preferably from 0.1 to 5 parts.

As known by those skilled in the art, the preparation of acrylic polymers can be carried out by solution, emulsion, or bulk polymerization procedures using well-known polymerization techniques, such as free radical, anionic, and cationic techniques. The copolymers can then be formed into hotmelt adhesives by removal of the solvent, coagulation of the latex, or melt-processing of the neat polymers.

The polymerization may be conducted in the presence of one or more organic solvents and/or in the presence of water. Suitable organic solvents or mixtures of solvents are alkanes, such as hexane, heptane, octane, and isooctane; aromatic hydrocarbons, such as benzene, toluene, and xylene; esters, such as ethyl, propyl, butyl and heptyl acetate; halogenated hydrocarbons, such as chlorobenzene; alkanols, such as methanol, ethanol, iso-propanol, ethylene glycol, and ethylene glycol monomethyl ether; ethers, such as diethyl ether and dibutyl ether; or mixtures thereof.

In one advantageous embodiment of the process, the polymerization reactions proceed in an ethyl acetate solvent under AIBN catalysis. In other variant, the polymerization reactions are conducted under acid or base catalysis. As acids, it is possible to use any Lewis-acidic compounds. The reactions take place preferentially with p-toluenesulfonic acid or itaconic acid. As bases, it is possible to use any Lewis base. The reactions take place preferentially with catalysis by 4-vinylaniline or sodium acetate.

The acrylic polymers prepared will generally have an average molecular weight ($M_w$) of from 10,000 to 2,000,000 g/mol, more preferably between 100,000 and 700,000 g/mol. The $M_w$ is determined by gel permeation chromatography (GPC) or matrix-assisted laser desorption/ionization mass spectrometry (MALDI-MS).

In a preferred embodiment of the photoinitiator, both ethylene oxide and the urethane, or urea, carbonate, or siloxane functional group are used together as a spacer to connect a UV-reactive group and a polymerizable group. Specifically, the ethylene oxide is directly bonded to the benzophenone or acetophenone moiety, and the carbamate, urea or carbonate groups is bonded to polymerizable styrenic C=C double bond group. Preferably, either acetophenone or benzophenone is used as the UV-reactive group and the C=C bond from m-TMI® is used as the polymerizable group. The structure of such a spacer provides high UV-crosslinking efficiency and high thermal stability to the acrylic polymers.

The acrylic polymers can be prepared by polymerizing monomer mixtures of components (a)-(e). Alternatively, preparation of the UV-crosslinkable acrylic polymers may comprise a two step reaction: (1) preparing acrylic polymers that have pendant isocyanate functionality by using m-TMI® or MOI as a co-monomer in polymerization reactions; and then (2) reacting the pedant isocyanate groups with hydroxyl- or amine-functionalized benzophenone or acetophenone. In this two-step process, only a limited number of monomers from components (a), (b), (c), and (d) can be used since pedant isocyanate group may react with functional groups such as alcohol, amine, and acid.

To be used as hotmelt PSAs, the acrylic polymers must be free of the solvent. For this purpose the copolymers prepared as described above are concentrated to a solvent content of less than 2% by weight, preferably less than 0.5% by weight. This process takes place preferably in a concentration extruder, such as vent extruder, ring extruder, single-screw extruder, or twin-screw extruder, which are known to the skilled worker.

The adhesive may also comprise various other additives, such as plasticizers, tackifiers, and fillers, all of which are conventionally used in the preparation of hotmelt PSAs. As tackifying resins to be added, it is possible to use any known tackifying resins described in the literature. Representatively, mention may be made of pinene resins, indene resins, and rosins, their disproportionated, hydrogenated, polymerized, and esterified derivatives and salts, the aliphatic and aromatic hydrocarbon resins, terpene resins, terpene-phenolic resins, C5 resins, C9 resins, and other hydrocarbon resins. Any desired combinations of these or other resins may be used in order to adjust the properties of the resultant adhesive in accordance with the desired final properties.

In general it is possible to use any resin which is compatible with the corresponding acrylic polymers; reference may be made in particular to all aliphatic, aromatic, alkylaromatic hydrocarbon resins, hydrocarbon resins based on straight monomers, hydrogenated hydrocarbon resins, functional hydrocarbon resins, and natural resins. Explicit reference may be made to the depiction of the state of the art in the "Handbook of Pressure Sensitive Adhesive Technology" by Donatas Satas (van Nostrand, 1989).

In a further advantageous development one or more plasticizers, such as low molecular weight acrylic polymers, phthalates, whale oil plasticizers, or plasticizer resins, are added to the acrylic HMPSAs.

The acrylic HMPSAs may further be blended with one or more additives such as aging inhibitors, antioxidants, light stabilizers, ozone protectants, fatty acids, resins, nucleating agents, blowing agents, compounding agents, and/or accelerators.

They may further be mixed with one or more fillers such as fibers, carbon black, zinc oxide, titanium dioxide, solid or hollow glass (micro)beads, microbeads of other materials, silica, silicates, and chalk. The addition of blocking-free isocyanates is also possible.

For the inventive process it may further be of advantage to add compounds to the acrylic HMPSAs that facilitate subsequent crosslinking. For this purpose the copolymers may optionally be blended with crosslinkers. Examples of suitable crosslinkers are functional acrylates. Preferred substances in accordance with the inventive process in which crosslinking occurs under radiation are, for example, difunctional or trifunctional acrylates, and difunctional or polyfunctional urethane acrylates. It is, however, also possible here to use any further difunctional or polyfunctional compounds which are familiar to the skilled worker and are capable of crosslinking acrylic polymers. For optional thermal or moisture crosslinking it is possible to use blocked difunctional or polyfunctional isocyanates or other functional groups.

One further development that makes the process of the invention particularly advantageous for the production of HMPSAs is that all additives are either blended to the neat acrylic polymers in melt, or more efficiently, added into the solutions of the copolymers at the end of the polymerization reactions. Upon the removal of the solvent, the mixtures are concentrated to give HMPSAs.

In most pressure sensitive uses, a hotmelt adhesive is applied to a backing or substrate before crosslinking. The adhesive is formulated preferably to provide a composition that can be heated to render a coatable fluid on the substrate. Commonly used industrial coating temperatures are in the range of 80-180° C. Typically, the HMPSAs of this invention have melt viscosities between 1000-500,000 cPs, preferably between 5000-100,000 cPs at those application temperatures.

Application of the HMPSAs may be accomplished using any conventional means, such as roller, slot orifice, spray, or extrusion coating. The substrate can be in a form of films, tapes, sheets, panels, foams, and the like; and can be made of materials such as paper, fabric, plastic (polyesters, PE, PP, BOPP, and PVC), nonwoven fibers, metals, foil, glass, natural rubber, synthetic rubber, wood, or plywood. This listing is not intended to be conclusive. If a coated substrate is to be used in the form of a roll, the back of the substrate is usually coated with a release coating to prevent the adhesive from adhering to the reverse side of the substrate. If a substrate is to be coated with the adhesive on both sides and rolled, a strippable paper or other protective means is laid over the adhesive on one side to prevent that adhesive from adhering to the adhesives on the other. In some uses, a second substrate may be applied directly to the adhesive.

A pressure sensitive adhesive film may be formed by applying the hotmelt to a release liner, such as silicone coated paper or plastic film, and then after irradiation, the adhesive may be stripped from the release liner and used as a film. Alternatively, the adhesive can be coated onto a release liner, laminated and transferred to a substrate.

The hotmelt PSAs of the invention can be crosslinked in air or nitrogen by irradiation with UV light in the range from 200 to 500 nm, preferably 250 to 320 nm. Irradiation may be done immediately while the adhesive compositions are still in melt, or after they cool to room temperature.

The irradiation is done for a period of time sufficient to transform the low cohesive composition into an elastomeric adhesive of higher plasticity. The exact length of exposure will be dependent upon the nature and intensity of the radiation, the amount of photoinitiator [the component (e)], the polymer composition, adhesive formulation, the thickness of the adhesive film, environmental factors, and the distance between the radiation source and the adhesive film. The dosage or the length of exposure is controlled by the belt speed. It may be appropriate to adapt the lamp output to the belt speed or to shade off the belt partly, in order to reduce its thermal load.

The actual radiation used can be actinic light from any source, provided it furnishes an effective amount of UV radiation, since the adhesive compositions of the invention generally exhibit their maximum sensitivity to wavelengths in the ultraviolet range. Suitable sources of radiation are carbon arcs, mercury-vapor arcs, fluorescent lamps with special ultraviolet light emitting phosphors, electronic flash lamps and the like, lasers of specific wavelengths, or combinations of those. Preferred lamps are the electrodeless microwave powered lamps from Fusion Systems, or commercially customary high or medium pressure mercury lamps with an output of, for example, from 80 to 240 W/cm.

In addition, the acrylic HMPSAs described in accordance with the invention may be crosslinked with electron beams. This type of crosslinking can also take place in addition to the UV crosslinking. Electron beam curing takes place by means of ionizing radiation.

The following examples are provided for illustrative purposes only, without wishing to subject it thereby to any unnecessary restriction.

EXAMPLES

Each of the adhesive samples was tested according to the following test methods for pressure sensitive tapes, some of which were developed by the Pressure Sensitive Tape Council (PSTC).

Preparation of Coatings

The procedure to apply a hotmelt pressure sensitive adhesive or a neat copolymer to a substrate and cure it under UV irradiation was as follows. A labcoater with two heatable rolls was used to apply the adhesive. The adhesive was heated to 150° C. and coated onto a 2 mil thick silicone-coated PET release liner. The adhesive on the liner was then irradiated at a line speed of 35 feet per minutes under H-bulb (Fusion Systems) with a dosage of UV-A 585 mJ/cm², and UV-B 512 mJ/cm². The film was then laminated and transferred to a polyethylene terephthalate substrate (Mylar®, DuPont) and conditioned at 23° C. and 50% relative humidity. Unless otherwise indicated, the adhesive film thickness was 3.5 mil.

Gel Fraction

The percent gel fraction was used as an indication of crosslinking level and photoinitiator efficiency. A sample of UV-irradiated acrylic polymer (or formulated adhesive) was separated from the silicone release liner and weighted to the nearest 0.1 mg. The sample was then placed in a glass jar and immersed into toluene for 24 to 48 h. The difference in the sample masses before and after toluene extraction gave the gel fraction, as a percentage of the mass fraction of the copolymer that is insoluble in toluene. If the sample is a formulated adhesive, the mass of any toluene-soluble component needs to be subtracted from the initial weight.

Shear Adhesion Sear adhesion was measured according to Procedure A, PSTC-107, adapted as follows. All test samples of the acrylic polymers were UV irradiated according to the procedure described above. The shear adhesion was measured under a shear load of 1 kg on a 12×25 mm area, applied after wetting out the test panel for 15 min. All testing was performed at 23° C. and 50% relative humidity.

Peel Adhesion

Peel adhesion at 180° between the substrate and the adherend test was measured according to Test method A, PSTC-101, adapted as follows. All test samples of the acrylic polymers were UV-irradiated according to the procedure described above. The peel strength was measured after wetting out a stainless steel panel for 15 min.

Loop Tack

Loop Tack was measured according to Test Method B, PSTC-16, adapted as follows. A loop tack tester was used for the measurement. All test samples of the acrylic polymers were UV-irradiated according to the procedure described above. The adhesive was coated on 2 mil PET film backing and the size of a specimen strip was 125 mm×24 mm.

Shear Adhesion Failure Temperature (SAFT)

All test samples of the acrylic polymers were UV-irradiated according to the procedure described above. The SAFT measurement was performed by placing a 25×25 mm bonded test specimen in an oven at 120° F. under a shear load of 1 kg (15 min wet out at room temperature before applying the load). The oven temperature was the raised in 1° F. increment every 1 min and the temperature at which the bond failed was recorded. If the bond did not fail, the test automatically ended at 375° F. at which time the oven will begin to cool down.

Example 1

A solution of 4-(2-hydroxyethoxy)benzophenone (5.0 g, 0.02 mol) in chloroform (anhydrous, 60 mL) was stirred at room temperature under $N_2$. 3-Isopropenyl-α,α-dimethylbenzyl isocyanate (m-TMI®) (4.2 g, 0.02 mol) and dibutyltin dilaurate (0.04 g, 0.06 mmol) were added subsequently. The reaction process was monitored by FTIR and was completed when the isocyanate peak (~2260 cm⁻¹) disappeared. The solvent was then removed under vacuum at room temperature and the product was collected as light yellow liquid with a quantitative yield. The identity of this compound was confirmed by ¹H NMR to have the following structure (IIA):

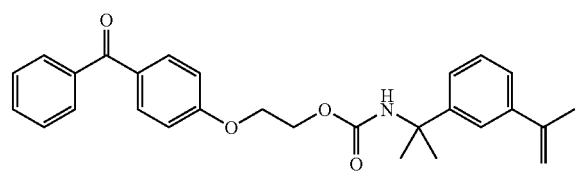

Example 2

A solution of 1-[3-(4-benzoylphenoxy)propyl]-1,1,3,3,-tetramethyldisiloxane (5.0 g, 0.013 mol) and allyl methacrylate (1.7 g, 0.013 mol) in toluene (anhydrous, 50 mL) was stirred at room temperature. Platinum-cyclovinylmethylsiloxane complex in cyclic methylvinylsiloxanes (15 mg) was added and the reaction mixture was continuously stirred for about 24 h. The reaction process was monitored by FTIR until the disappearance of the SiH peak (~2119 cm⁻¹). The solvent was then removed under vacuum at room temperature and the product was collected as a light yellow liquid with a quantitative yield. The identity of this compound was confirmed by ¹H NMR to have the following structure (IV):

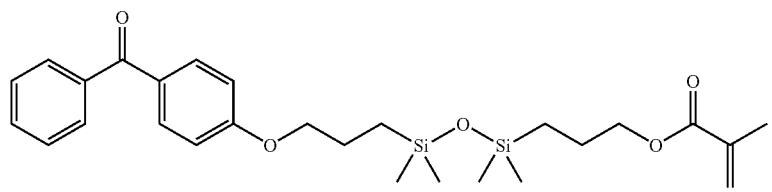

Example 3

A solution of 4-(2-hydroxyethoxy)benzophenone (5.0 g, 0.02 mol) in chloroform (anhydrous, 60 mL) was stirred at room temperature under $N_2$. 2-Isocyanatoethyl methacrylate (MOI) (3.2 g, 0.02 mol) and triethylamine (0.5 g, 5.0 mmol) were added subsequently. The reaction process was monitored by FTIR and was completed when the isocyanate peak (~2260 cm$^{-1}$) disappeared. The solvent was then removed under vacuum at room temperature and the product was collected as a light yellow liquid with a quantitative yield. The identity of this compound was confirmed by $^1$H NMR to have the following structure (V):

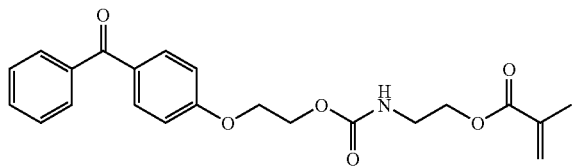

Example 4

A solution of 4,4'-methylenebis(phenyl isocyanate) (MDI) (5.1 g, 0.02 mol) in toluene (100 mL) was stirred at room temperature under $N_2$. Hydroxypropyl methacrylate (2.9 g, 0.02 mol) and triethylamine (1.0 g, 9.9 mmol) were added subsequently. A white precipitate formed slowly over 12 h. THF (anhydrous, 50 mL) was added and the solution turned clear and colorless. 4-(2-Hydroxyethoxy) benzophenone (5.0 g, 0.02 mol) was added and the mixture was stirred for an additional 12 h. After removal of all insoluble by-products by filtration, the solution was concentrated (~20 mL) under vacuum at room temperature and a small amount of hexane was added (~10 mL). An off-white crystalline solid was obtained from the solution after overnight standing at room temperature. The identity of this compound was confirmed by $^1$H NMR to have the following structure (VI):

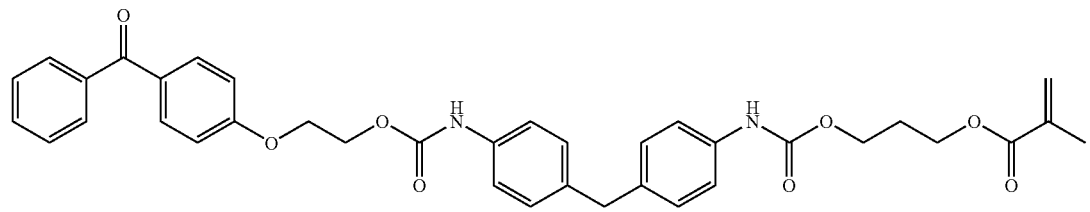

Example 5

A solution of 4,4'-methylenebis(phenyl isocyanate) (MDI) (10 g, 0.04 mol) in toluene (anhydrous, 150 mL) and triethylamine was stirred at room temperature under $N_2$. Hydroxypropyl methacrylate (5.8 g, 0.04 mol) was added slowly. A white precipitate formed slowly over 12 h. THF (anhydrous, 50 mL) was added and the solution turned clear and colorless. 4-Hydroxybenzophenone (7.9 g, 0.04 mol) was added and the mixture was stirred for an additional 12 h. After removal of all insoluble by-products by filtration, the solvents were removed and the solid was extracted with methanol. The obtained methanol solution dried under vacuum at room temperature to give a crude product. Recrystalization in toluene/hexane (1:2) gave an off-white crystalline solid. The identity of this compound was confirmed by $^1$H NMR to have the following structure (VII):

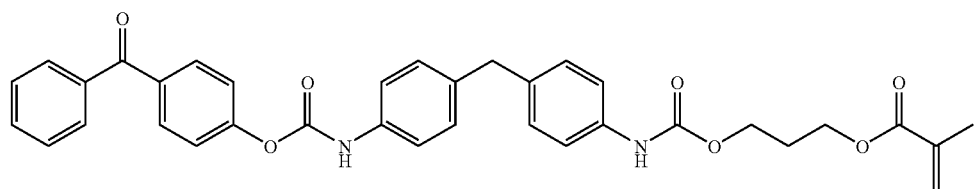

Example 6

A solution of 4-benzophenone (10.0 g, 0.05 mol) in chloroform (anhydrous, 60 mL) was stirred at room temperature under $N_2$. 2-Isocyanatoethyl methacrylate (MOI) (8.0 g, 0.05 mol) and triethylamine (1.0 g, 10.0 mmol) were added subsequently. The reaction process was monitored by FTIR until the disappearance of the isocyanate peak (~2260 cm⁻¹). The solvent was then removed under vacuum at room temperature and the product was collected as a light yellow liquid with a quantitative yield. The identity of this compound was confirmed by ¹H NMR to have the following structure (VIII):

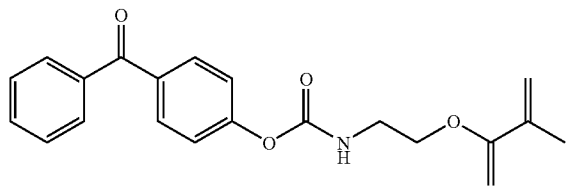

Example 7

A solution of 4-(2-hydroxyethoxy)benzophenone (2.0 g, 8.3 mmol), methacrylic anhydride (2.5 g, 16.2 mmol), and 4-(dimethylamino)pyridine (DMAP) (0.2 g, 1.6 mmol) in methylene chloride (100 mL) was stirred at room temperature under N₂ for 12 h. The reaction mixture was washed with aqueous solution of sodium hydroxide twice and distilled water twice. Solvent was removed by distillation at 30° C. The reaction solvent was then removed under vacuum at room temperature and the product was collected as a viscous light yellow liquid. The identity of this compound was confirmed by ¹H NMR to have the following structure (IX):

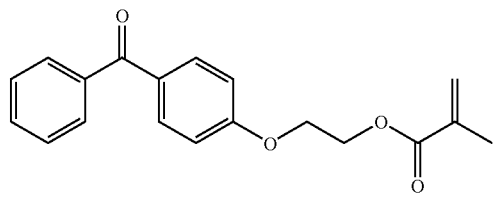

Example 8

Several acrylic polymers containing different polymerizable photoinitiators were prepared by solution polymerization. Each copolymer comprised a mixture of acrylic monomers: 70 pphm (parts per hundred part monomer by weight) of ethylhexyl acrylate (2-EHA), 20 pphm of methyl acrylate (MA), 10 pphm of 1-vinyl-2-pyrrolidinone (NVP), and 0.8 ppm of polymerizable photoinitiators. The reagents and procedure were the following (Table 1):

TABLE 1

| Monomer Mix | pphm | Weight (g) |
|---|---|---|
| 2-Ethylhexyacrylate | 70.0 | 210.0 |
| Methyl acrylate | 20.0 | 60.0 |
| 1-Vinyl-2-pyrrolidinone | 10.0 | 30.0 |
| Photoinitiator monomer | 0.8 | 2.4 |
|  | Total | 302.4 |
| Initial Charge |  |  |
| Monomer mix |  | 50.0 |
| Ethyl acetate |  | 100.0 |
| Vazo-64 |  | 0.5 |

TABLE 1-continued

| Monomer Mix | pphm | Weight (g) |
|---|---|---|
| Monomer Slow Add |  |  |
| Monomer mix Initiator Slow Add |  | 252.4 |
| Vazo-64 |  | 1.0 |
| Ethyl acetate | | 150.0 |
| Scavenger Slow Add | | |
| Lupersol 554, M50 | | 1.0 |
| Ethyl acetate | | 25.0 |
| | Total | 579.9 |
| | Solid | 53% |

The initial charge was heated to reflux and held for 15 min. While maintaining reflux, addition of the remaining monomer mix was started and continued over 2 h; simultaneously, the addition of the initiator was started and continued over 3 h. At the completion of the initiator addition the reaction was held at reflux for an additional 3 h. The scavenger catalyst was the added over 1 h and the reaction mixture was held at reflux for 2 h after the addition was completed. After cooling to 25° C., the content were analyzed for residual 2-EHA. If residual 2-ethylhexyacrylate was greater than 0.1%, additional scavenger was added for over 1 h. The resulting solution had a solid content of 53%. After the solvent was stripped of under vacuum at 60-70° C., the hotmelt pressure sensitive adhesive (neat polymer) was obtained with $M_w$ of approximately 1.0-1.8×10⁵ determined by GPC. Several acrylic polymers (A through G) were prepared by this procedure and their compositions are shown in Table 2.

TABLE 2

| | Composition | | | | | | |
|---|---|---|---|---|---|---|---|
| | A | B | C | D | E | F | G |
| 2-EHA, pphm | 70 | 70 | 70 | 70 | 70 | 70 | 70 |
| MA, pphm | 20 | 20 | 20 | 20 | 20 | 20 | 20 |
| NVP, pphm | 10 | 10 | 10 | 10 | 10 | 10 | 10 |
| Photoinitiator, pphm | 0.8 (IIA) | 0.8 (IV) | 0.8 (V) | 0.8 (VI) | 0.8 (VII) | 0.8 (VIII) | 0.8 (IX) |

Example 9

This example describes the gel fraction and shear strength results for the copolymers prepared in Example 8. The samples were tested following the procedures described above. The results are given in Table 3. All acrylic polymers showed reasonable gel fractions and shear adhesions. Polymer A had the highest UV crosslinking efficiency and shear adhesions. Polymer A203 and A258 were two UV-curable acrylic polymers commercially available from BASF Aktiengesellschaft.

TABLE 3

| Polymer | Gel fraction | Shear, 4 psi, 70° F. (12 mm × 25 mm × 1 kg), S.S |
|---|---|---|
| A | 72% | 65 h |
| B | 69% | 23 h |
| C | 70% | 27 h |
| D | 71% | 19 h |
| E | 67% | 24 h |
| F | 67% | 16 h |

TABLE 3-continued

| Polymer | Gel fraction | Shear, 4 psi, 70° F. (12 mm × 25 mm × 1 kg), S.S |
|---|---|---|
| G | 62% | 2.5 h |
| A258 UV | 70% | 12.3 h |
| A203 UV | 53% | 9.4 h |

Example 10

This example describes the viscosity, peel adhesion, and loop tack of some of the acrylic polymers prepared in Example 8. The samples were tested following the procedures described above. The results are shown in Table 4. All the polymers demonstrate comparable peel adhesion and loop tack.

TABLE 4

| Polymer | Viscosity cp, at 135° C. | Peel, 1 bf, S.S/, 20 min, 12 in/min | Loop Tack lb/in$^2$ |
|---|---|---|---|
| A | 45,900 | 4.8, AF | 7.23 |
| C | 18,400 | 4.6, AF | 6.21 |
| D | 32,500 | 4.5, AF | 5.90 |
| A258 UV | 59,700 | 4.8, AF | 5.75 |

Example 11

This example describes SAFT of some of the acrylic polymers prepared in Example 8. The samples were tested following the procedures described above. The results are given in Table 5. Polymer A had very high SAFT and its polymer specimens did not failed at the highest temperature of the test method.

TABLE 5

| Polymer | SAFT 2 psi, 1°/min, 5 mm × 25 mm × 1 kg |
|---|---|
| A | >190° C. |
| C | >150° C. |
| A258 | 115° C. |

Example 12

This example describes the thermal stability of the acrylic polymers prepared in Example 8. For this study, the test samples were not UV irradiated. The polymer samples were heated at 150° C. for 24 h. The viscosity changes of the samples before and after heating were measured using Brookfield and were used as criteria for the thermal stability of the copolymers. The testing results are listed in Table 6. Most polymers, except polymer E and F, exhibited good thermal stability below 150° C. for 24 h.

TABLE 6

| Polymer | Δη, 24 h, at 150° C. |
|---|---|
| A | 5% |
| B | 2% |
| C | 3% |
| D | 9% |
| E | Gelled |
| F | Gelled |
| G | 7% |
| A258 | 26% |

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A photoinitiator having the structural formula

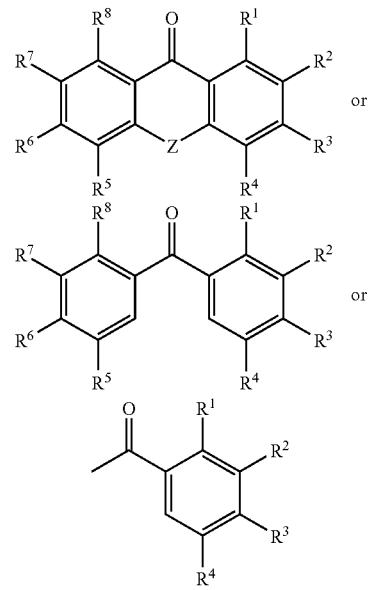

where
- Z is S, O, $CH_2$, or NH,
- $R^{1-8}$ are independently H, Cl, Br, I, F, $C_{1-24}$ alkoxy, $C_{1-24}$ alkyl, or aryl; and wherein at least one of $R^{1-8}$ must comprise a —W—X—Y group, where
- W is a $C_{1-12}$ oxyalkylene,
- X comprises tetramethyldisiloxane, and
- Y is —$R^9$—C($R^{10}$)=$CH_2$, where $R^9$ is a linear or branched $C_{2-10}$ alkylene or $C_{2-10}$ oxyalkylene, or arylene or derivative thereof, and $R^{10}$ is H or $CH_3$.

2. A photoinitiator having the structural formula

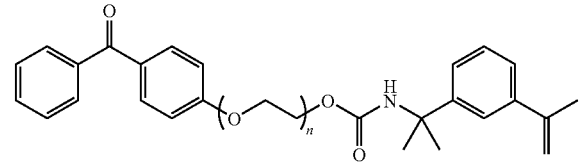

where n=1-12.

3. The photoinitiator of claim 2 wherein n=1.

4. A photoinitiator having the structural formula

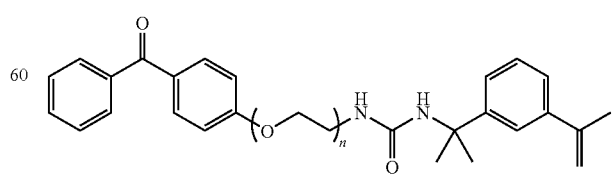

where n=1-12.

5. The photoinitiator of claim 4 wherein n=1.

6. A photoinitiator having the structural formula

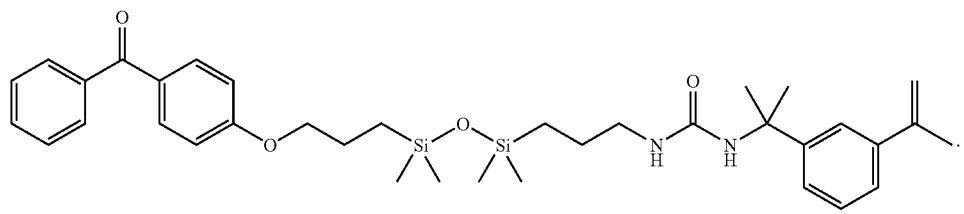

7. A UV curable acrylic polymer comprising the following monomer components:
  (a) from about 70 to about 95 parts by weight of acrylic or methacrylic acid derivative of the formula $CH_2=CH(R^1)(COOR^2)$, where $R^1$ is H or $CH_3$ and $R^2$ is a $C_{1-20}$ alkyl chain,
  (b) 0 to about 30 parts by weight of an acrylic or methacrylic acid derivative of the formula $CH_2=CH(R^1)(COOR^2)$, where $R^1$ is H or $CH_3$ and $R^2$ is an hydroxyl-functional $C_{1-20}$ alkyl chain,
  (c) 0 to about 20 parts by weight of an acrylic or vinyl compound containing a carboxy or anhydride functional group,
  (d) 0 to about 30 parts by weight of acrylic or vinyl compounds containing an amine, amide, urethane, epoxide or isocyanate functional group and
  (e) from about 0.01 to about 15 parts by weight of a photoinitiator having the structural formula

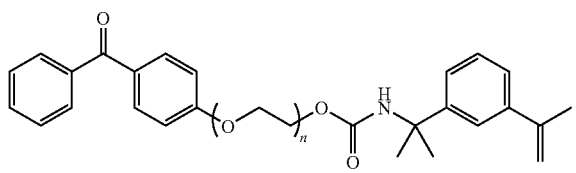

where n=1-12.

8. A UV curable acrylic polymer comprising the following monomer components:
  (a) from about 70 to about 95 parts by weight of acrylic or methacrylic acid derivative of the formula $CH_2=CH(R^1)(COOR^2)$, where $R^1$ is H or $CH_3$ and $R^2$ is a $C_{1-20}$ alkyl chain,
  (b) 0 to about 30 parts by weight of an acrylic or methacrylic acid derivative of the formula $CH_2=CH(R^1)(COOR^2)$, where $R^1$ is H or $CH_3$ and $R^2$ is an hydroxyl-functional $C_{1-20}$ alkyl chain,
  (c) 0 to about 20 parts by weight of an acrylic or vinyl compound containing a carboxy or anhydride functional group,
  (d) 0 to about 30 parts by weight of acrylic or vinyl compounds containing an amine, amide, urethane, epoxide or isocyanate functional group and
  (e) from about 0.01 to about 15 parts by weight of a photoinitiator having the structural formula

[structure]

where n=1-12.

9. A UV curable acrylic polymer comprising the following monomer components:
  (a) from about 70 to about 95 parts by weight of acrylic or methacrylic acid derivative of the formula $CH_2=CH(R^1)(COOR^2)$, where $R^1$ is H or $CH_3$ and $R^2$ is a $C_{1-20}$ alkyl chain,
  (b) 0 to about 30 parts by weight of an acrylic or methacrylic acid derivative of the formula $CH_2=CH(R^1)(COOR^2)$, where $R^1$ is H or $CH_3$ and $R^2$ is an hydroxyl-functional $C_{1-20}$ alkyl chain,
  (c) 0 to about 20 parts by weight of an acrylic or vinyl compound containing a carboxy or anhydride functional group,
  (d) 0 to about 30 parts by weight of acrylic or vinyl compounds containing an amine, amide, urethane, epoxide or isocyanate functional group and
  (e) from about 0.01 to about 15 parts by weight of a photoinitiator having the structural formula

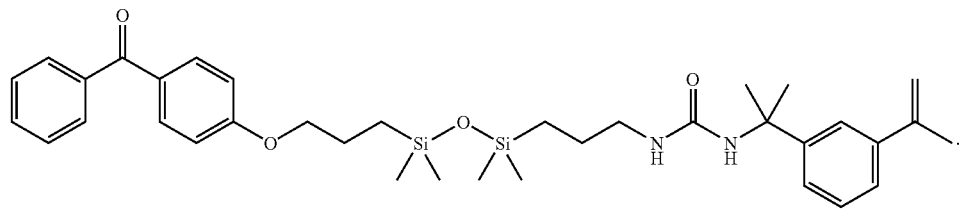

10. A UV curable hot melt pressure sensitive adhesive comprising
(a) from about 70 to about 95 parts by weight of methyl acrylate, methyl methacrylate, n-butyl acrylate, 2-ethylhexyl acrylate, and/or isooctyl acrylate,
(b) 0 to about 30 parts by weight of hydroxyethyl acrylate and/or hydroxypropyl acrylate,
(c) 0 to about 20 parts by weight of acrylic acid or maleic anhydride,
(d) 0 to about 30 parts by weight of 1-vinyl-2-pyrrolidinone (NVP), t-octyl acrylamide, 2-(tert-butylamino) ethyl methacrylate (t-BAEM), acrylamide, glycidyl methacrylate, 3-Isopropenyl-α, α-dimethylbenzyl isocyanate (m-TMI®), or a compound of the following formula

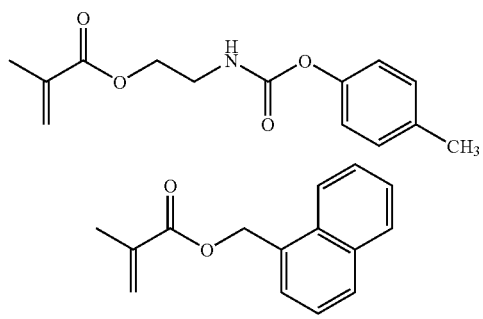

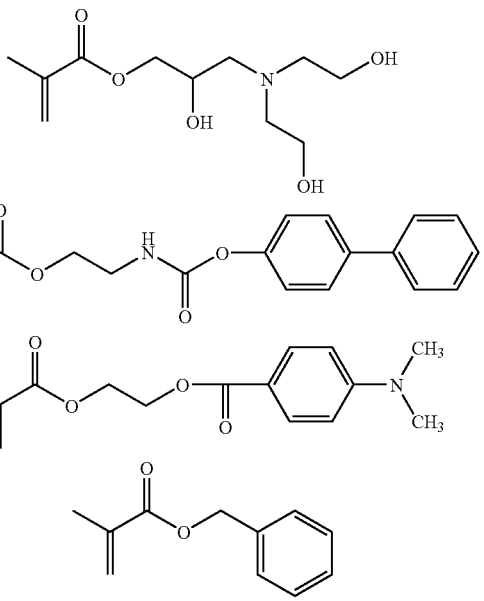

and
(e) from about 0.01 to about 15 parts by weight of a photoinitiator selected from the group consisting of

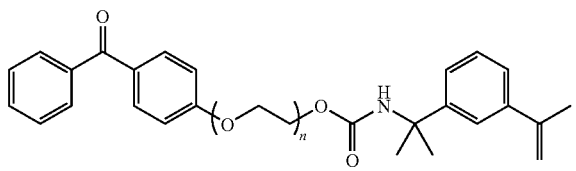

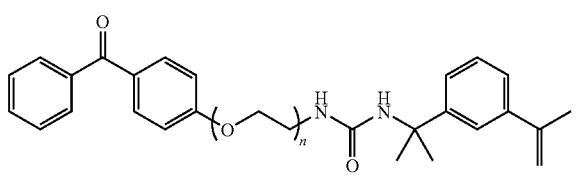

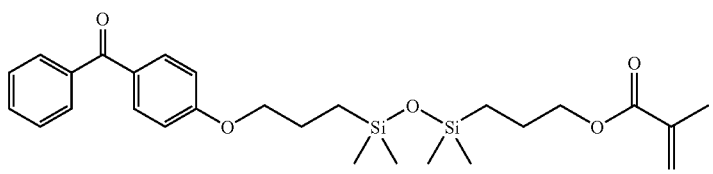

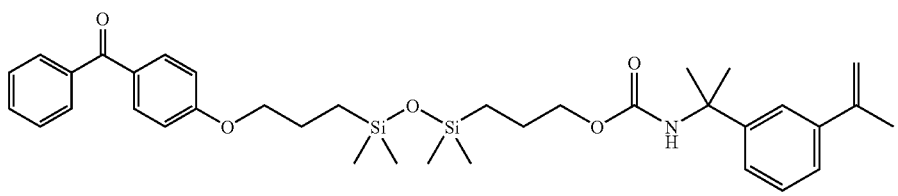

and
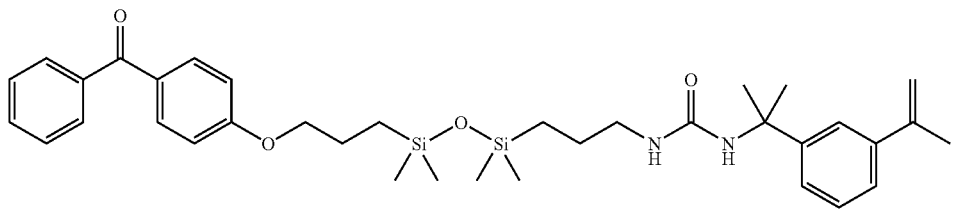
where n=1-12.
11. The adhesive of claim 10 wherein component (e) of the acrylic polymer is
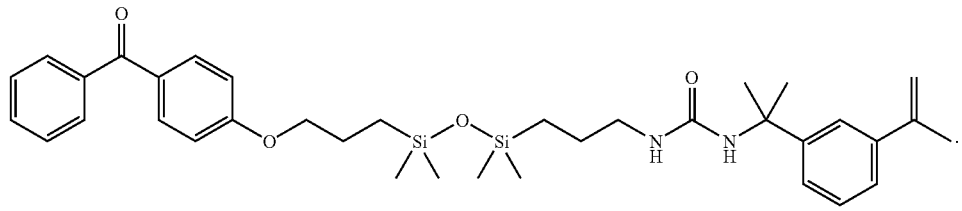
where n=1-12.
12. The adhesive of claim 10 wherein component (e) of the acrylic polymer is
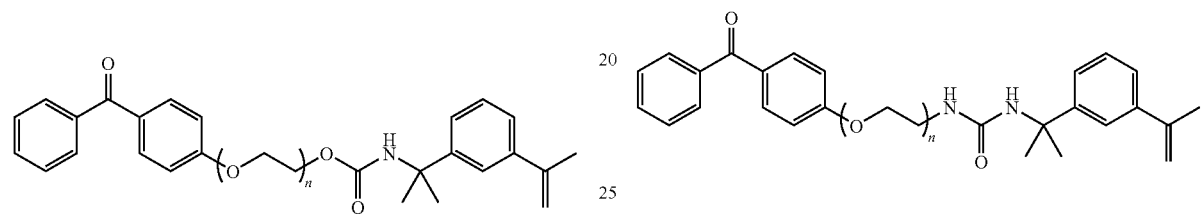
where n=1-12.
13. The adhesive of claim 10, wherein component (e) of the acrylic polymer is
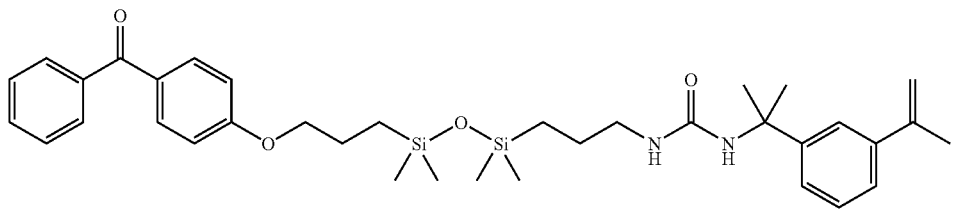
* * * * *